United States Patent [19]

Clements et al.

[11] Patent Number: 5,079,165
[45] Date of Patent: Jan. 7, 1992

[54] PRODUCTION OF THE *E. COLI* LT-B ENTEROTOXIN SUBUNIT IN *S. TYPHI*

[75] Inventors: John D. Clements, New Orleans; Sawsan E. El-Morshidy, Metarie, both of La.

[73] Assignee: Praxis Biologics, Inc., Rochester, N.Y.

[21] Appl. No.: 212,998

[22] Filed: Jun. 29, 1988

[51] Int. Cl.$^5$ .................. C12N 1/21; C12N 15/03; C07H 15/12; C07K 15/00
[52] U.S. Cl. .................. 435/252.8; 435/172.3; 435/91; 435/320.1; 435/879; 424/93; 424/92; 536/27; 935/12; 935/29; 935/72; 530/403
[58] Field of Search .................. 435/172.3, 253; 258/252.8, 252.3; 424/92, 93, 252.8, 320.1; 536/27; 530/403

[56] References Cited

U.S. PATENT DOCUMENTS 3,856,935 12/1974 Germanier ............... 424/92
4,237,224 12/1980 Cohen et al. ............ 435/68
4,304,863 12/1981 Collins et al. .......... 435/172
4,356,170 10/1982 Jennings et al. .
4,411,888 10/1983 Klipstein et al. ........ 424/92
4,550,081 10/1985 Stocker et al. .

FOREIGN PATENT DOCUMENTS 0060129 9/1982 European Pat. Off. .

OTHER PUBLICATIONS

Dallas et al., J. Bacteriol. 139:850-858 (1979).
Mekalanos et al., Proc. Nat'l Acad. Sci., U.S.A. 79:151-155 (1982).
Moseley et al., J. Bacteriology 144:444-446 (1980).
Pearson et al., Proc. Nat'l Acad. Sci. U.S.A. 79:2976-2980 (1982).
Finkelstein and LoSpalluto, J. Exp. Med. 130:185 (1969).
Mekalanos et al., Nature 306:551-557 (1983).
Yamamoto et al., J. Bacteriol., vol. 148, pp. 983-987, Dec. 1981.
Yamamoto et al., J. Bacteriol., vol. 150, pp. 1482-1484, Jun. 1982.
Yamamoto et al., J. Bacteriol., vol. 152, pp. 506-509, Oct. 1982.
Bolivar and Backman, Methods in Enzymology 68:245 (1979).
Clements and Finkelstein, Infect. Immun. 21:1036 (1978).
Finkelstein, Crit. Rev. Microbiol. 2:553 (1973).
Formal et al., Infect. Immun. 34:746 (1981).
Germanier and Furer, J. Infect. Dis. 131:553 (1975).
Gill et al., Infect. Immun. 33:677 (1981).
Gilman et al., J. Infect. Dis. 136:717 (1977).
Klipstein and Engert, Infect. Immun. 23:592 (1979).
Klipstein and Engert, Infect. Immun. 31:144 (1981).
Klipstein et al., Infect. Immun. 32:1100 (1981).
Klipstein et al., J. Infect. Dis. 147:318 (1983).
Neill et al., Infect. Immun. 41:1056 (1983).
Roberts and Lauer, Methods in Enzymology 68:473 (1979).
Sack and Sack, Infect. Immun. 11:334 (1975).
Sanchez et al., Fems Microbiol. Lett. 14:1 (1982).
Sansonetti et al., Infect. Immun. 34:75 (1981).
Sheer et al., Gastroenterology 65:895 (1973).
Shine and Dalgarno, Nature 254:34 (1975).
Wahdan et al., Bull. W.H.O. 58:469 (1980).
Yamamoto et al., J. Bacteriol. 148:983 (1981).
Clements et al., 83rd Annual Meeting of the American Society for Microbiology, New Orleans, Mar. 6-11, Abstract No. B49, p. 31 (1983).

*Primary Examiner*—Elizabeth C. Weimar
*Assistant Examiner*—Christopher S. F. Low
*Attorney, Agent, or Firm*—Pennie & Edmonds

[57] ABSTRACT

Methods and compositions are provided for the cloning and expression of plasmids bearing genes coding for the non-toxic subunit of the heat-laible enterotoxin (LT-B) of *E. coli*. These plasmids may be cloned into stable avirulent strains of *Salmonella typhi* and used to make oral bivalent vaccines. Such vaccines may be used to prevent typhoid fever and cholera-like enterotoxin-induced diarrheal disease.

8 Claims, 4 Drawing Sheets

PRODUCTION OF THE E. COLI LT-B ENTEROTOXIN SUBUNIT IN S. TYPHI

This application is a continuation of application Ser. No. 652,377 filed Sept. 20, 1984, now abandoned, which is a continuation-in-part of an application Ser. No. 628,873, filed July 9, 1984 now abandoned, which is incorporated herein by reference.

INTRODUCTION

This invention relates to a process for the production of a non-toxic B subunit of the heat-labile enterotoxin (LT-B) from a human isolate of an enterotoxigenic strain of *Escherichia coli*. This process utilizes recombinant DNA techniques, in which the requisite gene sequence is inserted by means of a suitable DNA vector into a non-pathogenic microbial strain. The use of a stable avirulent *Salmonella typhi* strain as a host cell for this DNA vector is described, and the resulting recombinant strain may be formulated as a bivalent oral vaccine to provide protection against both typhoid fever and cholera-like enterotoxin-induced diarrheal disease.

BACKGROUND OF THE INVENTION

Enterotoxigenic Bacteria and Diarrheal Disease

Acute diarrheal disease due to the temporary colonization of the small intestine by enterotoxigenic strains of certain bacteria is a major health problem of global significance. Among the responsible bacteria, perhaps the most widely recognized is *Vibrio cholerae*. Less well known but of greater practical significance are particular strains of *Escherichia coli* (*E. coli*) which, together with rotavirus, produce acute diarrheic episodes that are fatal each year to an estimated 10 million infants living in underdeveloped tropical countries [Black et al., Lancet i: 141 (1981)]. These *E. coli* strains also generally account for a high incidence of the acute diarrhea that afflicts visitors to tropical regions.

Both *Vibrio cholerae* and the enterotoxigenic *E. coli* strains produce their diarrheic effects through production of an enterotoxin. The cholera enterotoxin has been isolated and purified to homogeneity by Finkelstein [Crit. Rev. Microbiol. 2: 553(1973)]. Furthermore, Finkelstein and LoSpalluto [J. Exp. Med. 130: 185 (1969)] have separated a protein subunit from the cholera toxin that has reduced biological activity. What has emerged from these and from other studies is the finding that the cholera enterotoxin is an 84,000 dalton protein that consists of an A and a B subunit.

The A suounit (28,000 daltons) is responsible for the biological effects of the toxin but is incapable of binding to its target receptors alone. Through the action of sulfhydryl reagents, the A subunit may be cleaved into two polypeptide chains, with molecular sizes of 7,000 and 21,000 daltons. Of these chains only the larger, designated $A_1$, is active.

The B subunit, which has a size of 56,000 daltons, is essential for the expression of the activity of tne A subunit. Apparently it acts by binding to a target cell and then facilitating penetration by the active A subunit. Finkelstein et al. [J. Immunol. 113: 145 (1974)] have shown that tne B subunit consists of non-covalently associated subunits that can be dissociated by vigorous treatment with sodium dodecyl sulfate or at low pH with urea into five polypeptide chains.

The effects of cholera toxin have been demonstrated by Sneer et al. [Gastroenterology 65: 895 (1973)] in rabbit 3ejunum. In that system, the toxin causes a blood to lumen unidirectional flux of sodium. As a result, the intestinal fluid becomes low in protein, $Mg^{++}$ and $Ca^{++}$, and high in $K^+$, $Na^+$ and $HCO^-_3$, compared to normal serum levels. With these ionic changes, there is a concomitant outflowing of water to the lumen, for the maintenance of osmotic equilibrium with the blood plasma.

The precise structure of the cholera toxin receptor is unknown, but it appears to be a glycolipid. This observation is based upon a finding by King and van Heyningen [J. Infect. Dis. 131: 643 (1975)] that the binding of cholera toxin to membranes is inhibited by various glycosphingolipids. Of the compounds of this type examined, $G_{MI}$ (galactosyl-N -acetylgalactosaminyl(sialyl)-galactosylglucosylceramide) was most potent.

Once cholera toxin binding occurs, there is a stimulation of adenylate cyclase activity and a locking of that enzyme in the activated state. The result is an increase in intracellular levels of cAMP that in some way gives rise to the above ionic changes.

Enterotoxic strains of *E. coli* also mediate their diarrheic effects through the production of enterotoxins. These toxins are of two types, one of which is a relatively low molecular weight species of 2,000 daltons. Because ir survives treatment at 100° C., this species is referred to as the heat-stable toxin (ST). A second toxin that is heat labile (LT) is remarkably similar to the cholera toxin.

As shown by Gill et al. [Infect. Immun. 33: 677 (1981)], *E. coli* LT consists of the same type and number of subunits as the cholera toxin, and the corresponding subunits have approximately the same molecular weights. As with cholera toxin, the B subunits of LT attach to intestinal mucosal glycolipid receptors, thus permitting penetration of the cell by the biologically active A subunit. The sequence of events from that point on is also similar. Most importantly, Clements and Finkelstein [Infect. Immun. 21: 1036 (1978)] have shown that *E. coli* LT is immunologically related to both the A and B subunits of cholera enterotoxin.

Enteric Fever

Typhoid fever occurs in many of the same areas of the world in which cholera and the diseases caused by the enterotoxigenic *E. coli* bacteria are endemic. Thus, a vaccine that would be effective in preventing all of these conditions would be highly desirable.

The principal agent responsible for typhoid fever, *S. typhi*, is usually orally ingested, after which it passes through the lymphoid tissues into the bloodstream. From the blood, it is removed by the cells of the reticuloendothelial system (e.g., the liver, spleen, mesenteric lymph nodes and bone marrow).

During the incubation period, populations of *S. typhi* increase, especially in the spleen and liver, and after ten days to two weeks they again infiltrate the vascular system. At that point, clinical disease ensues. While improved sanitary conditions have reduced the incidence of typhoid fever to some extent, the mortality rate among those who contract the disease remains at about ten percent.

Immunological Approaches to the Prevention or Cure of Enterotoxigenic Diarrheal Disease and Typhoid Fever The most practical means for combating the widespread morbidity and mortality caused by microbial toxin-induced diarrheal disease would be protective vaccination. In the case of the enterotoxigenic *E. coli* strains, three approaches might be taken.

First, somatic antigens could be used for immunization. Killed or attenuated bacteria could be employed for this purpose, but this approach entails some risk and is likely to be of limited effectiveness. If the cell killing or attenuation is incomplete, clinical disease may develop. Even if this does not occur, protection will be imperfect since antigenically dissimilar somatic serotypes will not be recognized.

Secondly, Acres et al. [Infect. Immun. 25: 121 (1979)] have shown that pilus-mediated anchorage is a prerequisite for the induction of diarrheal disease by certain strains of enterotoxin-secreting *E. coli*. Thus, interference with cellular adhesion would have a prophylactic effect. Such interference could be produced by vaccination with pilus antigens, but again any protection so conferred would be applicable only to antigenically similar bacteria. Morgan et al. [Infect. Immun. 22: 771 (1978)] have detected multiple antigenically dissimilar pilus antigens among animal and human enterotoxigenic *E. coli* strains.

Finally, it should be possible to vaccinate animals with the enterotoxin itself. The immunity thus established would provide protection against active challenge with any of the relevant *E. coli* strains that produce the toxin. For reasons not clearly understood, immunization with LT toxin appears to provide protection against strains producing both LT and ST. There would not be protection against strains that produce only ST, but these strains are in the minority. Klipstein and Engert [Infect. Immun. 23:592 (1979)] have described the active immunization of rats with purified LT protein.

Although immunization may be achieved through the use of LT itself, the use of the biologically inactive B subunit (LT-B) alone should be almost as effective, and of course safer. The efficacy of this approach has been shown in rats by Klipstein and Engert [Infect. Immun. 31:144 (1981)]. Such immunization should also confer protection against cholera-induced diarrheic attacks, because of the immunological relationship between LT and the cholera enterotoxin described above.

Klipstein et al. have also immunized rats with ST coupled to LT [Infect. Immun. 32:1100 (1981)] or to the LT-B protein [J. Infect. Disease 147:318 (1983)]. A patent based on such conjugates and their use as vaccines has been issued to Klipstein *et al.* [U.S. Pat. No. 4,411,888].

For immunization against typhoid fever, mutants of *S. typhi* that have defects in galactose metabolism have proven to be most effective and safe as vaccines. One such mutant, deficient in the enzyme uridine diphosphogalactose-4-epimerase and designated *S. typhi* strain Ty21a, was first proposed as a typhoid vaccine by Germanier and Fürer [J. Infect. Dis. 131:553-558 (1975)]. Subsequent studies by Gilman et al. [J. Infect. Dis. 136:717-723 (1977)] and by Wahdan et al. [Bull. W.H.O. 58:469-474 (1980)] have shown that strain Ty21a is in fact a safe, highly effective live oral vaccine for typhoid fever.

Recombinant DNA Technology

In current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in the segment of foreign DNA that is to be inserted, the two DNA molecules may be covalently linked by an enzyme known as a ligase. General methods for the preparation of such recombinant DNA molecules have been described by Cohen and Boyer in U.S. Pat. No. 4,237,224. Other useful general methods have been described by Collins and Hohn in U.S. Pat. No. 4,304,863. Because of their broad utility, these patents are hereby incorporated by reference.

Once prepared, recombinant DNA molecules can be used to produce the product specified by the inserted gene sequence only if a number of conditions are met. Foremost is the requirement that the recombinant molecule be compatible with, and thus capable of autonomous replication in, the host cell. Much recent work has utilized *Escherichia coli* (*E. coli*) as a host organism because it is compatible with a wide range of recombinant plasmids. Depending upon the vector/host cell system used, the recombinant DNA molecule is introduced into the host by transformation, transduction or transfection.

Detection of the presence of recombinant plasmids in host cells may be conveniently achieved through the use of plasmid marker activities, such as antibiotic resistance. Thus, a host bearing a plasmid coding for the production of an ampicillin-degrading enzyme could be selected from unaltered cells by growing the host in a medium containing ampicillin. Further advantage may be taken of antibiotic resistance markers where a plasmid codes for a second antibiotic-degrading activity, at a site where the selected restriction endonuclease makes its cut and the foreign gene sequence is inserted. Host cells containing properly recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid for DNA transcription called a promoter. Alternatively, the foreign DNA may carry with it its own promoter, as long as it is recognized by the host. Whatever its origin, the promoter is a DNA sequence that directs the binding of RNA polymerase and therefore "promotes" the transcription of DNA to messenger RNA (mRNA).

Given strong promotion that can provide large quantities of mRNA, the ultimate production of the desired gene product will be dependent upon the effectiveness of translation from mRNA to protein. This, in turn, is dependent upon the efficiency of ribosomal binding to the mRNA. In *E. coli*, the ribosome-binding site on mRNA includes an initiation codon (AUG) and an upstream Shine-Dalgarno (SD) sequence. This sequence, containing 3-9 nucleotides and located 3-11 nucleotides from the AUG codon, is complementary to the 3' end of *E. coli* 16S rioosomal RNA (rRNA) [Shine and Dalgarno, Nature 254: 34 (1975)]. Apparently, ribosomal binding to mRNA is facilitated by base pairing between the SD sequence in the mRNA and the sequence at the 16S rRNA 3' end. For a review on maximizing gene expression, see Roberts and Lauer, Methods in Enzymology 68: 473 (1979).

The introduction of LT plasmids from enterotoxigenic *E. coli* strains of human and porcine origin into other bacteria has recently been demonstrated by Neill et al. [Infect. Immun. 41:1056 (1983)]. In that study, LT plasmids from *E. coli* were transferred by conjugation into *E. coli* K-12 strains and into strains of *Shigella flexneri*, *Shigella sonnei*, *Citrobacter freundii*, *Enterobacter cloacae*, *Klebsiella pneumoniae* and *Salmonella typhimurium*. Analysis of the *transconjugants* showed that in all cases the transferred plasmids were stably maintained in their hosts. LT gene expression measured by solid-phase radioimmunoassay varied widely, however, with maximal LT production occurring in *E. coli*.

Genetic engineering techniques can also be applied to produce the B subunit of LT. Dallas [European Patent Application Serial No. 0060129] has described the cloning of the gene coding for LT-B from an *E. coli* isolate of porcine origin. The cistron encoding the B subunit of LT was cloned into vector pJJS500 by cleaving EWD299 with EcoRI and ligating this DNA to EcoRI cleaved pJJS500. The application stated that a plasmid specifying LT-B production without apparent LT-A contamination was thus obtained. It should be pointed out that no evidence was presented to support this claim, no mention was made of in vivo or in vitro studies, and there was no indication ot successful antibody production, based on the gene product.

Yamamoto et al. [J. Bacteriol. 148:983 (1981)] have described the cloning of the LT-B gene from a human *E. coli* isolate into plasmid pBR322. Some expression of the gene product was detected by growing the modified bacterium in a radiolabeled amino acid mixture and then analyzing crude cell lysates by SDS polyacrylamide gel electrophoresis. No effort was made, however, to purify or characterize the LT-B protein, and it is not known whether the level of gene expression was significant.

In other studies, Sanchez et al. [FEMS Microoiol. Lett. 14:1 (1982)] cloned the LT-B gene from a human isolate into vector pACYC184. Again, the gene product was neither purified nor characterized. In all of these studies, the LT-B-producing plasmid was cloned into *E. coli*. The use of *E. coli* as a potential oral vaccine is unfavorable, because it tends to colonize principally in tne proximal small oowel and to retain most of the LT-B produced. Hence such a vaccine would be poorly immunogenic, although it can be the source of LT-B following cell disruption.

Bacteria that are non-virulent but which are invasive and which release appreciable quantities of genetically engineered protein products are superior immunogens. Formal et al. [Infect. Immun. 34:746 (1981)] have used such a bacterium, *Salmonella typi* Ty21a, as a host cell for a plasmid bearing the genes for the form I cell surface antigen of *Shigella sonnei*. Strain Ty21a is a stable mutant that lacks uridine diphosphogalactose epimerase. It is avirulent, because it has an incomplete outer wall polysaccharide structure and lyses in the presence of galactose. One of tne earliest uses of this kind of a mutant as a vaccine was described by Germanier in U.S. Pat. No. 3,856,935, although the mutant contained no recombinant plasmid.

SUMMARY OF THE INVENTION

Methods and compositions are provided for the cloning and expression in single-cell host organisms of genes coding for the non-toxic subunit of the heat-labile enterotoxin (LT-B) of an enterotoxigenic *E. coli* strain. Also described are methods for the selection and culturing of the modified LT-B-producing hosts. Through the use of a stable avirulent strain of *S. typhi* as a host, an oral bivalent vaccine may oe produced that provides protection against botn typhoid fever and cholera-like enterotoxin-induced diarrheal disease. As used in the present application, the term "chloera-like enterotoxin" shall mean cholera toxin and LT, as well as immunologically related enterotoxins naturally produced by *E. coli*, *Vibrio cholerae* or other gram-negative enteric bacilli, or produced by expression of the gene encoding cholera toxin, LT or such related enterotoxin in any microorganism, including strains of *Salmonella*, *Yersinia*, *Pseudomonas, Shigella, Citrobacter, Klebsiella,* and the like.

Unlike all other LT-B proteins that have been examined, whether derived from the chemical separation of the complete LT enterotoxin into its A and B subunits or from gene cloning, the LT-B produced by the recombinant plasmid pJC217 is non-toxic. This unusual freedom from toxic effects renders this invention uniquely suited for use in immunization procedures. To distinguish the LT-B of this invention from the toxic forms produced by other methods, it is designated LT-B non-toxic (LT-BNT).

BRIEF DESCRIPTION OF THE FIGURES

The present invention may be more readily understood by reference to the following FIGURES (not drawn to scale), wherein FIG. 1 is a schematic representation of the production of pDF82, an LT expression plasmid derived from pBR322, into which a 5.2 kb fragment containing the LT gene from an Ent plasmid of a human isolate of *E. coli* has been inserted;

FIG. 2 is a schematic representation of the construction of plasmid pDF87, through the insertion into the single HindIII site of pBR322 of a 0.8 kb fragment containing the LT-B gene and derived from plasmid pDF82 by HindIII excision;

FIG. 3 is a schematic representation of the production of plasmid pJC217 by insertion into the single HindIII site of pUC8 of a 0.8 kb fragment containing the LT-B gene and derived from plasmid pDF87; and FIG. 4 is a graphical representation of the lytic effects of galactose on *S. typhi* strains Ty21a and SE12.

DETAILED DESCRIPTION OF THE INVENTION

This invention relates to the use of gene splicing methodology to produce a plasmid containing the genes for a completely non-toxic biologically inactive subunit of the heat-labile enterotoxin (LT-B) of an enterotoxigenic bacterial strain. This invention further relates to the use of this plasmid to modify host bacterial cells. When *S. typhi* is used as a host, a bivalent oral vaccine may be formulated that can provide protection against both typhoid fever and cholera-like enterotoxin-induced diarrheal disease.

For the purpose of illustration, the procedures of this invention are detailed using one particular enterotoxigenic strain of *E. coli* as an exemplary source of LT-B genes. The fact that this microorganism was a human isolate may lead to a more potent antiserum for use in human beings. It must be emphasized, however, that there is strong cross reactivity between the comparable subunits of the toxins of many enterotoxigenic strains, whether they be of human, porcine or other origin. Thus this invention contemplates the potential use of any of them for this purpose, and the methods described herein are equally applicable to them all.

The methods of this invention entail a number of steps which, in logical sequence, include (1) identification and isolation of the gene encoding LT-B or a fragment thereof, (2) insertion of this gene or gene fragment into an appropriate cloning vehicle, (3) transfer of the genetically altered cloning vehicle into compatible single-cell host organisms, (4) selection and growth of properly modified hosts that can replicate and express the inserted gene sequences, (5) identification and purification of the gene product, and (6) use of the modified host organisms as an oral vaccine.

IDENTIFICATION AND ISOLATION OF LT GENES

The genes for the production of LT and its subunits are carried on plasmids (Ent plasmids) of enterotoxigenic *E. coli* strains. Thus a stool sample from a human being or other mammalian species afflicted with enterotoxin-induced diarrheic disease could serve as the crude source of the requisite gene sequences. Isolates from these sources may be grown in sufficient quantities using standard microbiological techniques that are well known to skilled practitioners in the art. Unfortunately, the ability to make enterotoxin confers no selective value upon the strains of *E. coli* that carry the Ent plasmid and produce enterotoxin. To monitor the transfer of the Ent plasmid into a stable laboratory strain such as *E. coli* K-12, a desiraole first step, it is thus necessary to mark the plasmid in some way.

In the illustrative embodiment of the present invention, the plasmids of a human isolate of *E. coli* H10407 were phenotypically tagged by transposition from an F'tslac::Tn5 plasmid as described by Sansonetti et al. [Infect. Immun. 34:75 (1981)]. The tagged plasmids were then transferred by conjugation to K-12 strain 711, and an LT-producing transcon3ugant was selected. This transconjugant contained two large plasmids of a size ($6 \times 10^7$ daltons) that Gyles et al. [J.Infect. Dis. 130:40 (1974)] had shown to be characteristic of plasmids producing enterotoxin in H10407.

Verification of the fact that the transconjugant produced LT was made by enzyme linked immunosorbent assay (ELISA), using antibodies produced against LT, and by biologic activity as determined by induction of morphologic alterations in cultured mouse Y-1 adrenal cells. The plasmids thus transferred were isolated by the cleared lysate technique of Bolivar and Backman [Methods in Enzymology 68:245-267 (1979)], and the specific LT gene sequences were isolated by restriction endonuclease cleavage.

In the illustrative embodiment, the purified ENT plasmid was cut with the restriction endonuclease Pst I, although any restriction enzyme or combination thereof could be employed so long as LT production (and subsequently LT-B production) is not destroyed by excision in the critical gene regions. The particular enzyme chosen would preferably be one that makes a single cut in the cloning vehicle used. Fulfillment of this second require may easily be achieved, since detailed restriction maps of many of the commonly used cloning vehicles are available.

Once appropriate cuts were made by Pst I in both the ENT plasmid and in the cloning vehicle, in this example plasmid pBR322, the LT gene fragment was ligated to the cloning vehicle by use of an appropriate ligating enzyme. Representative of ligating enzymes are the DNA ligases from *E. coli* and from bacteriophage T4. Such enzymes form new phosphodiester linkages in conjunction with ATP or NAD$^+$ as a cofactor.

Transformation of host bacterial cells with these recombinant DNA molecules containing the LT DNA fragments provides for the generation of copies of the requisite DNA, which can then be analyzed for production of LT as described above or used as a source of plasmid DNA for the subsequent isolation of specific gene fragments coding for production of LT-B only.

The insertion of the LT DNA restriction fragment into a cloning vector is easily accomplished when both the cut with the same restriction enzyme, since complementary DNA termini are thereby produced. If this cannot be accomplished, it may be necessary to modify the cut ends that are produced by digesting back single-stranded DNA to produce blunt ends, or by achieving the same result by filing in the single-stranded termini with an appropriate DNA polymerase. In this way, blunt end ligation with an enzyme such as T4 ligase may be carried out. Alternatively, any site desired may be produced by ligating nucleotide sequences (linkers) onto the DNA termini. Such linkers may comprise specific oligonucleotide sequences that encode restriction site recognition sequences. The cleaved vector and the LT DNA fragment may also be modified by homopolymeric tailing, as described by Morrow [Methods in Enzymology 68:3 (1979)].

Alternatives to the isolation of the LT gene, or fragments thereof, include but are not limited to the chemical synthesis of the gene sequences (if known) or the preparation of DNA that is complementary to the messenger DNA that encodes the LT gene.

IDENTIFICATION AND ISOLATION OF LT-B GENES

The gene fragment that codes for production of LT-B is adjacent to and downstream from the gene fragment that codes for production of LT-A. There are a number of restriction endonuclease sites within the LT gene that flank these specific gene fragments. Thus, a restriction enzyme is chosen which does not cut into the structural gene for the fragment under study (LT-B).

Once identified and isolated, the LT-B gene or gene fragment is inserted into an appropriate expression vector, which contains the necessary elements for transcription and translation of the inserted gene sequences. Since the promoter region for the LT-B subunit is normally furnished by the A subunit gene and this toxic product is to be avoided, the expression vehicle must contain its own promoter which can be read in sequence with the LT-B gene. Many plasmids into which the LT-B gene may be inserted contain such promoter regions, the tetracycline resistance gene of plasmid pBR322 and the lac. gene of plasmid pUC8 being only two examples.

The efficient transcription of the LT-B gene or gene fragment is further dependent upon the presence of specific initiation signals. One signal that is commonly employed is the ATG sequence. Sources of the ATG sequence include but are not limited to the cro or N genes of coliphage lambda and the *E. coli* tryptophan E, D, C, B or A genes. Such initiation sequences may be found among many other gene sequences into which the LT-B gene or fragment may be inserted, and they may be produced synthetically in the alternative.

Strong translation is tied to the availability of a Shine-Dalgarno (SD) sequence which facilitates efficient ribosomal attachment. Such SD sequences must be interposed between the promoter and the initiation signal, for efficient message readout. The objective high level production of the LT-B protein is thus dependent upon the insertion of the LT-B gene sequence downstream from promoter, SD and initiation sequences.

Numerous cloning vehicles meeting these requirements may be employed which include but are not limited to SV40, adenovirus, yeast, lambda gt-WES-lambda B Charon 4A and 28, lambda-gt-1-lambda B, M13-derived vectors such as pUC8, 9, 18 and 19, pBR313, 322 and 325, pAC105, pVA51, pACY177, pKH47, pACYC184, pUB110, pMB9, ColE1, pSC101, pML21, RSF2124, pCR1 or RP4.

Many of these cloning vehicles contain one or more marker activities that may be used to select for desired transformants, such as ampicillin and tetracycline resistance in pBR322 and ampicillin resistance and $\beta$-galactosidase activity in pUC8. Selection is greatly simplified when the host cells into which such vectors are inserted contain none of these activities, and one of the activities is lost by virtue of the insertion of the LT-B gene or gene fragment.

The transfer of the recombinant cloning vector into the host cell may be carried out in a variety of ways. Depending upon the particular vector/host cell system chosen, such transfer may be effected by transformation, transduction or transfection.

Depending upon the quality and quantity of the LT-B subunit produced, one or more clones may have to be prepared. In an illustrative embodiment of this invention, it was necessary to transfer the LT-B gene successively into two plasmids pBR322 and finally into plasmid pUC8. This multiple cloning sequence was necessitated by the fact that while all clones produced LT-B protein, the pBR322 recombinants produced low levels of LT-B (c.a. 1 mg/liter) and yielded toxic gene products. This toxicity was manifested by analysis in the Y1 adrenal cell assay system, which is described in detail in Section 6.2.2., infra. The basis of this toxicity was not understood, although the toxic LT-A subunit was not detectable in the preparation.

When the recombinant plasmid of this invention was transformed into *E. coli*, final LT-BNT production at levels 50 fold higher than present in wild type enterotoxigenic *E. coli* strains was achieved.

PURIFICATION OF LT-BNT

As produced in *E. coli* K-12, LT-BNT remains in the periplasmic space. Modified *S. typhi* retains about 50% of the LT-BNT that it produces as well. To free the desired subunit product of this invention in a high yield from either host it is thus necessary to disrupt the outer membrane. This is preferably accomplished by sonication, or by other mechanically disruptive means, such as the French pressure cell.

Cell disruption could also be accomplished by chemical or enzymatic means. Since divalent cations are often required for cell membrane integrity, treatment with appropriate chelating agents such as EDTA or EGTA might prove sufficiently disruptive to facilitate the leakage of LT-BNT from the cells. Similarly, enzymes such as lysozyme have been used to achieve the same result with proteins other than LT-BNT. That enzyme hydrolyzes the peptidoglycan backbone of the cell wall. In a specific *E. coli* embodiment of the invention described below, however, lysozyme caused a 60 percent loss of recoverable LT-BNT.

The application of osmotic shock could also be employed. Briefly, this could be accomplished by first placing the cells in a hypertonic solution which would cause them to lose water and shrink. Subsequent placement in a hypotonic "shock" solution would then lead to a rapid influx of water into the cells with an expulsion of the desired LT-BNT.

Once freed from the cells, LT-BNT may be concentrated by precipitation with salts such as sodium or ammonium sulfate, ultrafiltration or other methods well known to those skilled in the art. Further purification could be accomplished by conventional protein purification techniques including but not limited to gel filtration, ion-exchange chromatography, preparative discgel or curtain electrophoresis, isoelectric focusing, low temperature organic solvent fractionation, or countercurrent distribution. Purification is preferably carried out, nowever, by the exploitation of a peculiar property of LT, LT-B and LT-BNT—an affinity for binding to agarose.

Both the complete toxin and the B subunit bind tenaciously to the galaclosyl residues of agarose. Thus LT-BNT is oest purified by the selective retention of the subunit following the passage of a solution containing LT-BNT through an agarose column. Once bound and purged of other proteins by washing the column with buffer, the subunit may be freed oy passing a galactose-containing solution through the column. This affinity chromatographic technique works well with *E. coli* K-12 because it is a rough bacterial strain. Wild-type strains bind the LT-BNT produced to galactosyl residues in their outer membranes, and very little of the subunit can be recovered on agarose columns from these strains. Thus, while the technique has occasionally been successfully employed with wild-type strains, best results are obtained with *E. coli* K-12 into which the LT-BNT genes have been inserted.

PREPARATION OF AN ORAL BIVALENT VACCINE

An LT-BNT-producing *E. coli* recombinant strain produced by the method of this invention provides large quantities of the enterotoxin subunit, as fully described in copending U.S. patent application Ser. No. 628,873. This LT-BNT can be used to produce antibodies against LT-B, for immunotherapeutic, prophylactic, or diagnostic purposes. Such *E. coli* recombinant strains are unsuitable for use as oral vaccines, however, for two principal reasons. First, orally administered *E. coli* are non-invasive and become confined principally to the proximal small bowel. Secondly, *E. coli* recombinants retain the LT-BNT that they produce. As a result, immunological stimulation oy LT-B-producing *E. coli* strains would not be very effective.

To overcome these difficulties, plasmids containing the genes for LT-B can be inserted into hosts other then

*E. coli.* The primary requirements for alternative hosts are plasmid compatibility and safety. A host cell must be compatible to permit replication of the plasmid and expression of the LT-B gene. Furthermore, the host cell must be avirulent. A non-pathogenic strain could be used, or a pathogenic strain could be "attenuated" through prolonged in vitro propagation, or mutated.

Avirulent mutants can be produced by exposing pathogenic strains to ionizing or ultraviolet radiation, or to any of a number of mutagenic chemical compounds. A few of the compounds that could be used are N-nitrosodimethylamine, N-nitrosomethylurea, or N-methyl-N'-nitro-N-nitrosoguanidine. Of course, any useful mutant must be stable and must not revert to the virulent phenotype.

In a preferred embodiment of the present invention, *S. typhi* Ty21a was used as a host cell. Unlike *E. coli, S. typhi* is invasive, affecting the distal small bowel and entering the lymphoid tissues of a host. Thus, *S. typhi* disseminates to sites where its immunogenic potential is maximized. Strain Ty21a is avirulent because it lacks uridine diphosphate (UDP) -galactose-4-epimerase, an enzyme that is essential for galactose metabolism, and it also lacks the Vi antigen.

The absence of UDP-galactose-4-epimerase results in an incomplete cell wall lipopolysaccharide structure that in part explains the avirulence of the microorganism. An even more significant factor in the lack of pathogenicity of strain Ty21a is the fact that galactose taken up by the cells accumulates as galactose-1-phosphate and UDP-galactose [Germanier and Fürer, J. Infect. Diseases 131: 553-558 (1975)]. As a consequence, the cells lyse in the presence of galactose, which is ubiquitous in human beings and in other mammalian species.

An important advantage of the recombinant strain Ty21a, designated SE12, is that a vaccine based upon it is bivalent, conferring immunity against both typhoid fever and cholera-like enterotoxin-induced diarrheal disease.

The vaccine of this invention may be maintained in a staole storage form for ready use by lyophylization or by other means well known to those skilled in the art. For oral administration, the vaccine may be reconstituted as a suspension in buffered saline, milk, or any other physiologically compatable liquid medium. The medium may be made more palatable by the addition of suitable coloring and flavoring agents as desired.

Administration of the vaccine may be preceded by an oral dosage of an effective amount of a gastric acid neutralizing agent. While many compounds could be used for this purpose, sodium bicarbonate is preferred. Alternatively, the vaccine may be delivered in enteric coated capsules (i.e., capsules that dissolve only after passing through the stomach).

EXAMPLE

General Procedures for Recombinant Plasmid Preparation

In the present invention, the source of the LT-BNT gene was *E. coli* 711 (10407), a K-12 transconjugant containing the LT-ST plasmid of a human enterotoxigenic (-GO-TO-GL-)407. This strain was derived by phenotypically tagging the enterotoxin plasmid of *E. coli* H10407 by transposition from an F'ts lac::Tn5 plasmid and conjugally transferring the Tn5-tagged plasmid to *E. coli* K-12 strain 711.

The plasmid was cleaved by a restriction enzyme to yield a small DNA fragment containing the LT gene. The DNA fragment was then ligated into a pBR322 plasmid, to produce a plasmid designated pDF82. *E. coli* K-12 transformants harboring the plasmid were then selected on the basis of antibiotic resistance markers. LT production by the transformants was established through the use of an enzyme-linked immunosorbent assay and an adrenal cell assay system.

The cloned LT-B DNA region was identified and then twice recloned, first into a pBR322 plasmid to give plasmid pDF87, and then into the M13-derived cloning vector pUC8. The resultant recombinant plasmid, pJC217, was cloned after transformation into *E. coli* K-12 and selection by antibiotic resistance and the loss of an enzymatic activity marker. LT-BNT recovered from pJC217, which was immunologically indistinguishable from pDF87 and native LT-B but completely non-toxic, was then isolated from host cell lysates for use as an immunogen.

A detailed description of each step in the construction follows.

Conditions for Restriction Enzyme Digestions

The restriction enzymes used were the products of Bethesda Research Laboratories, Inc., Gaithersburg, Md. A unit of enzyme activity is defined as the amount of enzyme required to completely digest 1.0 ug of lambda DNA in one hour at an appropriate temperature and in a 50 ul total reaction mixture volume.

Digestions were carried out by incubating 2 ug of DNA with 10 units of enzyme at 37° C for 30 minutes in 20 ul of buffer. Reactions were stopped by heating to 70° C. for 5 minutes, and the overall conditions produced one cleavage per vector plasmid DNA molecule. For Pst I and Hind III, the buffer consisted of 50 mM Tris-HCl (pH 8.0), 10 mM $MgCl_2$ and 50 mM NaCl. Other reactions were carried out essentially as descrioed by the manufacturer.

Purification of DNA Digestion Products

Following restriction enzyme treatment of pDF87, the digestion mixture was subjected to electrophoretic separation in vertical gel slabs containing 1.2% low melting point agarose in 40 mM Tris, 0.2M sodium acetate and 2 mM EDTA (pH 7.8). Electrophoresis was carried out at 10 volts per cm, and the slabs were then stained with ethidium bromide and visualized under ultraviolet light, as described by Bolivar and Backman [Methods in Enzymology 245 (1979)].

The separated DNA fragments were then excised from the gel, the gel was melted, and the LT-B DNA fragment was extracted with phenol.

T4 DNA Ligation

Ligation reactions were carried out with T4 DNA ligase from Bethesda Research Laboratories, Inc., Gaitnersburg, Md. A unit of T4 DNA ligase activity is defined as the amount required to catalyze the conversion of 1 nmole of $^{32}PPi$ into $[/\beta\ ^{32}P]$-ATP at 37° C. in 20 minutes.

DNA ligations were performed using 10 units of enzyme per ug of DNA at 4° C for 18 hours. The buffer contained 66 mM Tris-HCl, 6.6 mM $MgCl_2$, 10 mM dithiothreitol and 66 uM ATP at pH 7.6.

To reduce recircularization, in some cases plasmid pBR322 was treated with alkaline phosphatase conjugated to Sepharose before ligation. The enzyme used was MATE-BAP from Bethesda Research Laboratories, Inc., Gaithersburg, Md. One unit of MATE-BAP is defined at the amount of enzyme that hydrolyzes 1 nmole of ATP in 30 min. at 37° C. The enzyme was used at a concentration of 500 units per ug of DNA at 65° C. for 1 hour in 10 mM Tris-HCl, pH 8.0. Following reaction, the enzyme was removed by centrifugal pelleting.

Transformation and Isolation of Recombinants

The transformation of host bacterial strains was carried out as described by Bolivar and Backman [Methods in Enzymology 68:245 (1979)]. Cells were made competent by incubation in 30 mM $CaCl_2$ at 0° C. for 20 minutes. Then 0.2 ml aliquots of 10X concentrated cells were added to DNA in 0.1 ml of cold ligation buffer supplemented with 30 mM $CaCl_2$ and incubateo at 0° C. for 1 hour. The cells were then heated to 37° C. for 2 minutes, held at room temperature for 10 minutes, and diluted into 4ml of Luria broth (L broth). Per liter, L broth contains 10 g of Bacto tryptone, 5 g of Bacto yeast extract, and 10 g of NaCl, all adjusted to pH 7.5 with 1 M NaOH.

After 3 hours of incubation at 37° C, transformants were selected on Trypticase soy agar [BBL Microbiology Systems, Cockeysville, Maryland] or YT plates, using appropriate antibiotics or enzymatic activity markers as described infra.

Methods for LT Gene Product Analysis

At each stage of the cloning procedure, the transformants were analyzed for the quality and quantity of LT or LT-B production by enzyme-linked immunosorbent assay (ELISA). To determine the toxicity of their gene products, the transformants were also analyzed by a mouse adrenal cell assay system in which cells exposed to enterotoxigenic E coli or to their toxins exhibit readily detectable morphological changes.

Enzyme-Linked Immunosorbent Assay (ELISA)

As described by Clements et al. [Infect. Immuno. 40:653 (1983)], clones to be analyzed were cultured overnight at 37° C in 20 ml of Trypticase soy broth [BBL Microbiology Systems, Cockeysville, Maryland], centrifuged, suspended in 2 ml of buffer containing 0.05 M Tris, 0.001 M EDTA, 0.003 M sodium azide and 0.2 M NaCl [pH 7.5], and disrupted by sonication with a Branson sonicator for 12 seconds at a power setting of 100–150 watts. The resultant lysates were clarified by centrifugation and serially diluted in pH 7.4 phosphate-buffered saline containing 0.05% Tween 20 (Polyoxyethylene sorbitan monolaurate) (PBS-Tween) for analysis.

ELISA was carried out using two basic methods. In one method the wells of polystyrene microtiter plates [Costar, Cambridge, Mass.] were precoated with 50 ug per ml of type III gangliosides [Sigma Chemical Co., St. Louis, Mo.] to improve the binding of the LT-B subunit and, hence, to increase sensitivity. The microtiter wells were then filled witn 0.2 ml a±iquots containing the diluted lysate samples and incubated for 1 hour at room temperature. Following the incubation, the microtiter wells were emptied and washed three times with PBS-Tween. The wells were then treated successively for one hour each at room temperature with monospecific goat hyperimmune antiserum to LT [Clements et al., Infect. Immun. 29:91 (1980)] and with rabbit anti-goat antiserum conjugated to alkaline phosphatase [Miles Research Laboratories], with three PBS-Tween washings following each addition.

Alkaline phosphatase analysis was then performed by adding 200 ul aliquots of 1 mg/ml p-nitrophenyl phosphate substrate in 10 percent diethanolamine buffer (pH 9.8), incubating the plates for 60 minutes at room temperature, stopping the reactions by the addition of 25 ul aliquots of 3 M NaOH, and measuring the results spectrophotometrically at 400 nm.

In some cases, a modification of the ELISA method of Holmgren and Svennerholm [Scand J. Immunol. 8, Suppl. 7: 111–118 (1978)] was used instead. Microtiter plates were precoated with type III gangliosides, and 100 ul aliquots of samples to be tested in PBS with 0.5% gelatin (PBS-G) were pipetted into the microtiter wells. The plates were then incubated at 37° C for 45 minutes, the wells were filled with PBS-G, incuoation was continued for anotner 30 minutes at 37° C, and the plates were washed with PBS-Tween. The wells were then treated successively for 45-minute periods at 37° C with 100 ul aliquots of PBS-G containing first antiserum to LT, and then antiserum directed against the anti-LT immunoglobulins that had been conjugated to horseradish peroxidase. Following each incubation period, the wells were washed three times with PBS-Tween.

Horseradish peroxidase analysis was then carried out with the use of o-phenylenediamine as a substrate. The substrate was prepared immediately before use by dissolving 1 mg of o-phenylenediamine (Sigma Chemical Co., St. Louis, Mo.) per 1 ml of 0.1 M sodium citrate buffer, pH 5.0. Then, an equal volume of a solution containing 1 ml of 0.3% $H_2O_2$ per 50 ul of the citrate buffer was added to yield a final 0.006% $H_2O_2$ concentration. Two hundred ul of the substrate was added to each well, the plates were incubated for 30 minutes at room temperature in the dark, and the peroxidase reaction was stopped by the addition to each well of 75 ul of 4M $H_2SO_4$. The results were determined spectrophotometrically by measuring absorbance at 492 nm.

ELISA employing horseradish peroxidase was considerably more sensitive than that using alkaline phosphatase. In other respects, however, the two systems were comparable.

Yl Adrenal Cell Enterotoxin Assay

Clarified cell lysates, prepared as described in Section 6.2.1. supra, were analyzed for toxicity in the mouse Yl adrenal cell system of Sack and Sack [Infect. Immun. 11: 334 (1975)]. Yl adrenal cells maintained in Ham's F10 medium with 12.5% horse serum, 2.5% fetal calf serum, and 40 ug per ul gentamycin were subcultured into 75 $cm^2$ culture dishes containing the same medium and incuoated at 37° C. until the cells reached confluency.

Once the cells were confluent, the medium was replaced by fresh medium containing serially diluted aliquots of LT-B-producing clone lysates, and the cultures were incubated further. After 18 to 24 nours of incubation, the cultures were examined with a phase contrast inverted microscope for cell morphology. Under the influence of LT toxin, the normally flat adrenal cells become rounded. The sensitivity of the assay is such that 5 as little as 0.2 ug of crude *E. coli* toxin or 10 pg of purified LT per 200 ul of medium may be detected.

Rat Ileal Loop Assay of Enterotoxin Activity

Using the method of Klipstein and Engert [Infect. Immun. 23:592–599 (1979)], weanling Sprague-Dawley rats (Charles River Breeding Laboratories, Wilmington, Mass.) were surgically prepared oy exposing the ileum and ligating 10-cm loops at the distal portion. Each animal was then challenged by direct inoculation with LT, LT-B or LT-BNT in 0.5 ml of sterile saline solution into the loop.

After 18 hours, the animals were sacrificed and the loops were examined for fluid accumulation. Data derived from the values from 5-8 rats at each enterotoxin concentration were expressed as fluid accumulation per centimeter of ileum. A positive response, denoted by a fluid accumulation of more than 50 ul/cm of ileum, was observed with as little as 1 ug of LT.

Preparation and Isolation of Specific LT-B-Producing Clones

Because of toxicity in the LT-B produced by the first clones, the LT-B gene was successively transferred into plasmid pBR322 and then into the M13mp7-derived pUC8 plasmid [Vieira and Messing, Gene 19:259 (1982)].

Isolation of pDF82

Figure 1:
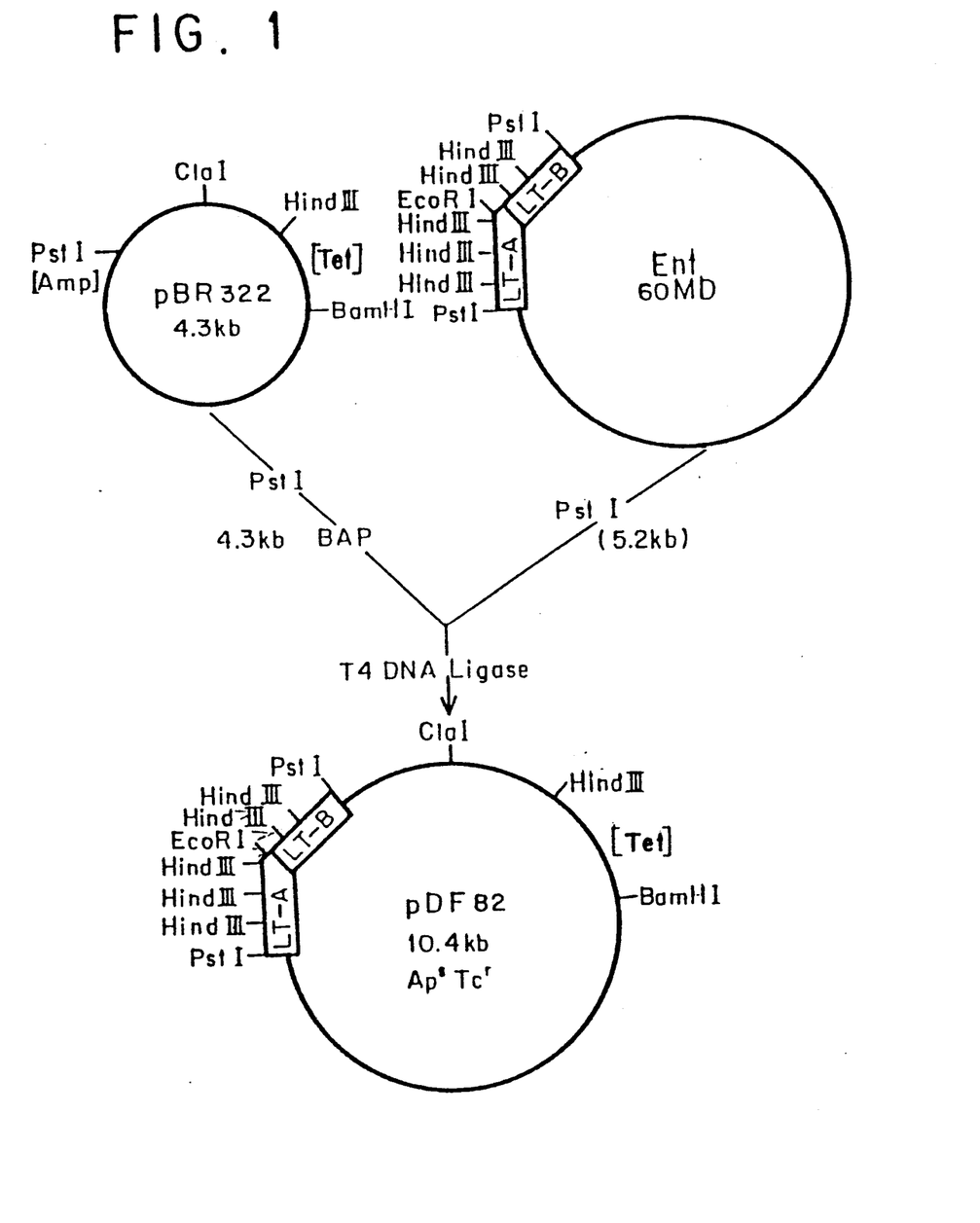

The $LT^+ST^+$ enterotoxin plasmid of human isolate H10407 was cleaved with the restriction enzyme Pst I, to yield a 5.2 Ko DNA fragment (see FIG. 1). This fragment, which contained the LT gene, was then inserted into plasmid pBR322 which had been cut with Pst I and treated with alkaline phosphatase. Ligation was carried out with T4 DNA ligase to produce a 10.4 Kb plasmid, designated pDF82. The ligation mixture was then used to transform $E\ coli$ MM294.

Plasmid pBR322 encodes both ampicillin and tetracycline resistance. When the plasmid is cut by the restriction enzyme Pst I and a DNA fragment is inserted, ampicillin resistance is lost, but not tetracycline resistance. These transformants were thus isolated by screening for ampicillin sensitivity ($Ap^s$) and tetracycline resistance ($Tc^r$) by growth, or inability to grow, in medium containing tnese antibiotics. After plating on Trypticase soy agar containing 25 ug per ml tetracycline, the cultures were incubated for 18 hours at 37° C. Growing colonies were then cloned in L broth, aliquots were spotted on Trypticase soy agar plates containing 100 ug per ml ampicillin and incubated for 18 hours at 37° C.

$Ap^sTc^r$ transformants were then assayed for LT production by the Y1 adrenal cell system and ELISA. Plasmid DNA was isolated from several $LT^+$ transformants by the method of Bolivar and Backman [Methods in Enzymology 68: 245 (1979)] and subjected to electrophoresis in 0.7% agarose. The conditions for electrophoresis and DNA visualization were as described in Section 6.1.2. above. One isolate, designated pDF82, was positive in both assay systems and showed only a single plasmid upon electropnoresis.

When recut with Pst I, plasmid pDF82 yielded only two fragments that corresponded to the 4.3 Kb pBR322 cloning vector and the 5.2 Kb LT-encoding DNA fragment. Subsequent analysis of the recombinant plasmid with Pst I, Eco RI, Hind III, Hinc II, Hinf I and Ava II confirmed the size of the DNA fragment and the absence of internal Pst I sites.

Isolation of PDF87

Figure 2:
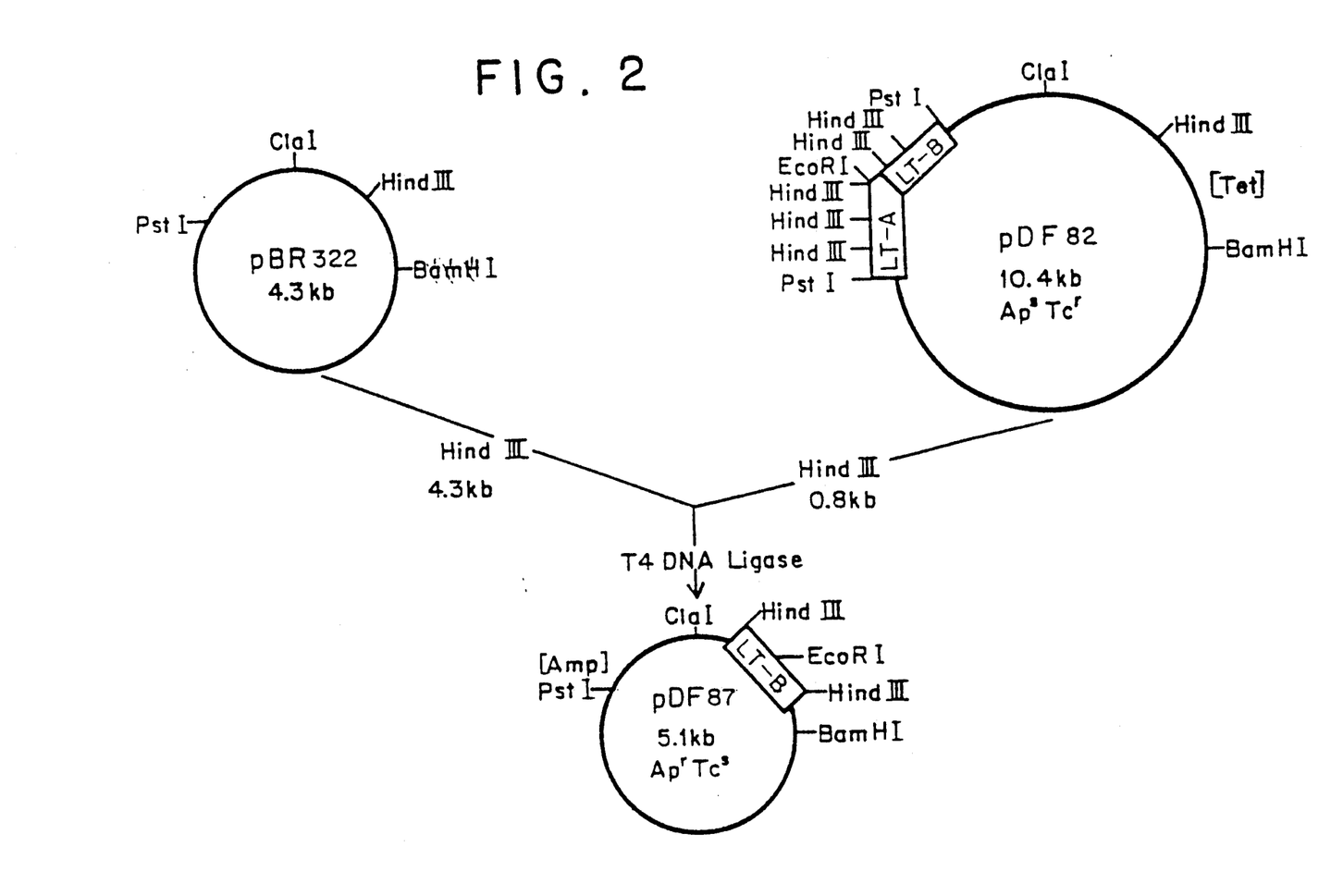

The cloned LT DNA region from pDF82 was recloned into tne single Hind III site in the tetracycline resistance gene of plasmid pBR322 (see FIG. 2). Plasmids pDF82 and pBR322 were cut with Hind III, mixed and joined by T4 DNA ligase. The ligation mixture was again transformed into $E.\ coli$ MM294, and transformants were selected on the basis of antibiotic resistance and sensitivity.

Because Hind III cleavage and DNA fragment insertion destroys tetracycline resistance but does not affect ampicillin resistance, $Ap^rTc^s$ cells were selected for. This was accomplished by a selection approach that was furtner enhanced by the use of cycloserine, which kills multiplying $E.\ coli$ cells. After 18 hours of incubation in L broth with 50 ug/ul ampicillin, the culture was diluted 1:100 into fresh medium containing 4 ug per ml tetracycline. After 45 minutes of incubation, D-cycloserine was added to a concentration of 100 ug per ml, and incubation was continued for an additional 2 hours.

The culture was then centrifuged, and the pellet was resuspended in 20 ml of L broth. After 3 hours of further incubation, 0.1-ml aliquots were plated on Trypticase soy agar with 50 ug per ml ampicillin, and the resultant colonies were isolated. The transformants were then assayed for the production of LT-B by ELISA and for the absence of LT-A by lack of toxicity in the Y1 adrenal cell assay. One clone largely meeting these requirements but retaining 1/1000 of the toxicity of LT from pDF82, on a weight basis, was designated pDF87. Tne reason for this toxicity was unclear, since no LT-A could.be detected in pDF87 by SDS polyacrylamide gel electrophoresis, ELISA, or gel filtration under dissociating conditions Treatment of pDF87 with Hind III split the DNA into two fragments—pBR322 and a smaller (0.8Kb) fragment coding for LT-B. Significantly, the 1.5 Kb Hind III gene fragment that codes for the production of LT-A was absent.

Isolation of pJC217

Figure 3:
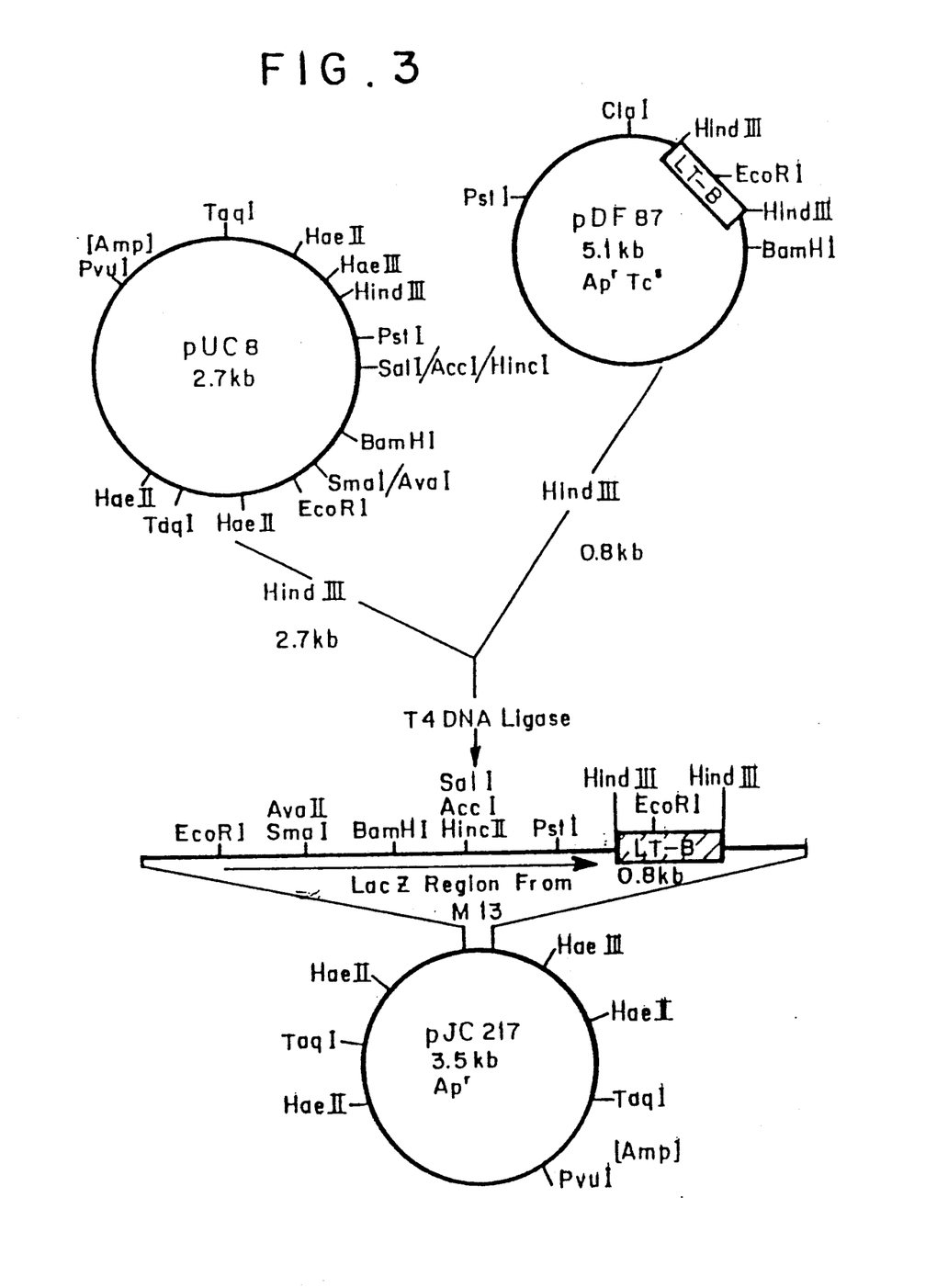

The cloned LT-B DNA from pDF87 was recloned into the single Hind III site of cloning vector pUC8 (see FIG. 3) This vector, constructed by Vieira and Messing [Gene 19: 259 (1982)], is derived from M13mp7. Plasmid pDF87 was cut with Hind III, and the 0.8 Kb LT-B DNA fragment was separated by electrophoresis in low melting point agarose (see section 6.1.2, supra) and extracted with phenol. pUC8 was then cleaved with Hind III, mixed with the purified LT-B gene fragment, ligated and transformed into an $E.\ coli$ K-12. Insertion of DNA fragments at the Hind III site of PUC8 disrupts the structural gene for $\beta$-galactosidase activity which, together witn unaltered ampicillin resistance in the plasmid, provides a basis for transformant selection.

Transformants were plated on YT plates (8 g Bacto Tryptone, 5 g NaCl, 5 g Yeast Extract and 1.5 g agar per liter of water) containing 100 ug per ml of ampicillin and supplemented with 200 ug per ml of 5-bromo-4-chloro-3-indoyl-$\beta$-D-galactoside (X-gal). As described by Rüthere [Mol.Gen.Genet. 178:475 (1980)], Xgal is a B-galactosidase substrate that in the presence of the enzyme turns from colorless to blue. Following incubation for 18 hours at 37° C. on Xgal-YT, colorless colonies (whose plasmid-associated $\beta$-galactosidase activity had been insertionally inactivated) were isolated.

Tne $Ap^r$ $\beta$-galactosidase$^-$ transformants were then assayed by ELISA for LT-BNT production. LT-BNT from one positive clone, designated pJC217, was then tested in Y1 adrenal cells, where it was found to be completely non-toxic. The bacterium harboring this plasmid was designated $E.\ coli$ strain JM83 (pJC217).

Insertion of Plasmid pJC217 Into Salmonella Typhi Strain Ty21a

Plasmid pJC217 from *E. coli* recombinant strain JM83 was purified by cesium chloride gradient centrifugation [Aovanced Bacterial Genetics: A Manual for Genetic Engineering, R.W. Davies et al., (eds.), Cold Spring Harbor Laboratory, New York (1980)] and then used to transform a streptomycin resistant mutant of *S. typhi* strain Ty21a. Transformation was carried out by the method of Bolivar and Backman [Methods in Enzymology 68: 245 (1979)], and transformants were selected on YT plates (8 g Bacto Tryptone, 5 g NaCl, 5 g Yeast Extract, and 1.5 g Agar per liter of $H_2O$) containing 100 ug/ml of streptomycin (Str) and 100 ug/ml of Ampicillin (Ap).

Following incubation on the YT plates for 18 hours at 37° C., transformant colonies were isolated and analyzed by ELISA assay (Section 6.2.1) for LT-BNT production. All $Ap^rStr^r$ transformants examined produceo LT-BNT. One isolate, designated strain SE12, was selected for further study. Plasmid DNA isolated from strain SE12 was shown by agarose gel electrophoretic analysis (Section 6.1.2) to have a mobility identical to that of plasmid pJC217 isolated from *E. coli* strain JM83. Furthermore, when digested with HindIII, the SE12 plasmid yielded the same two 4.3 kb and 0.8 kb DNA fragments produced by HindIII treatment of plasmid pJC217.

Figure 4:
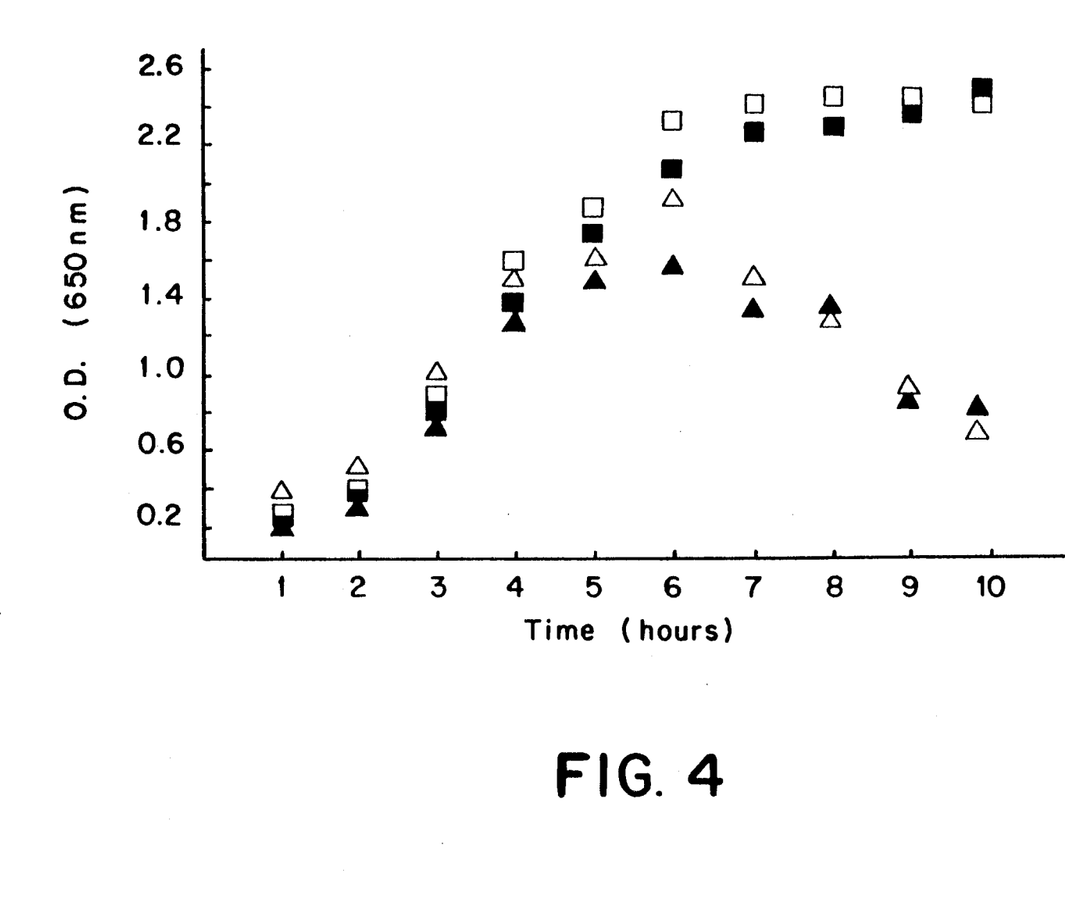

The utility of the SE12 strain as a bivalent oral vaccine is dependent upon the retention by the strain of its avirulent character. To determine whether the insertion of plasmid pJC217 into *S. typhi* Ty21a impaired the lytic response of the host organism to excess galactose (see Section 5.5), strain SE12 was observed in ML medium (10g tryptone, 5g NaCl and 5g yeast extract per liter of water) with or without 0.1% galactose. The results are shown in FIG. 4, wnere the growth of strain Ty21a, witn galactose (closed triangles) or without (closeo squares), is compared to the growth of strain SE12 with galactose (open triangles) or without (open squares). Lytic effects were detected as a decrease in the turbidity of the cell suspensions, measured spectrophotometrically at 650 nm.

As shown in FIG. 4, both strains underwent extensive lysis in the presence of 0.1% galactose. The insertion of plasmid pJC217 into strain Ty21a caused no diminution of the galactolytic response.

Recovery of LT-BNT

Growth of E. Coli K-12 Containing the pJC217 Plasmid

Subculturing of strain JM83 (pJC217) produces two types of colonies One, designated type 0, is small, raised and opaque in appearance. The other, designated type T, is larger, flat and translucent. It is important for the production of LT-BNT to utilize only type T colonies, since they produce 50–100 times as much LT-BNT as type O colonies. Because type 0 colonies can arise spontaneously from the T type, a single type T colony should be selected.

The choice of medium for the propagation of *E. coli* strain JM83 (pJC217) is not critical, and Trypticase soy broth, ML medium and the CAYE medium of Evans will suffice. In one embodiment of this invention, the organism transformed by plasmid pJC217 was streaked confluently on a 10x1.5 cm culture dish containing Trypticase soy agar with 100 ug/ml of ampicillin, to stabilize the plasmid. After incubation for 18 hours at 37° C., each plate contained a sufficient quantity of cells to serve as an innoculum for 10 liters of growth medium.

After the incubation, bacteria from the Trypticase soy agar plates were harvested with 5 ml of sterile 0.85 percent NaCl and used to inoculate CAYE medium with 0.5% glucose at a level of approximately $10^6$ CFU per ml. CAYE medium consists of 20 g of Casamino Acids, 6 g of Yeast Extract, 2.5 g of NaCl, 8.71 g of $K_2HPO_4$ and 1 ml of trace salts (5% $MgSO_4$, 0.5% $MnCl_2$ and 0.5% $FeCl_3$) per liter of distilled water. Following inoculation, the cultures were incubated with agitation at 37° C. for 18-24 hours.

Cell Disruption

Cells from the incubation medium were collected by centrifugation at 5,000 xg for 20 minutes at 4° C. The supernatant fluids were discarded into Clorox disinfectant, and the cell pellets were suspended in a minimal volume of buffer containing 0.05M Tris, 0.001M disodium EDTA, 0.003M sodium azide, and 0.2M NaCl, pH7.5 (TEAN biffer). These cell suspensions were then pooled and stored frozen at $-60°$ C. until needed.

The freezing and thawing of the cells generally provides sufficient disruption of *E. coli* K-12 for LT-BNT recovery. Mechanical disruptive techniques such as the use of sonication or a French press could be applied as long as scrupulous care was taken to avoid the generation of heat in the sample. Disruption by sonication or by a French press was also effective for *S. typhi* SE12. Lysozyme should be avoided, since final LT-BNT recoveries from *E. coli* strain JM83 (pJC217) with it as a lytic agent were decreased by 60 percent.

By swirling the storage containers for a minimum time in a 37° C. water bath, the frozen cell suspensions were rapidly thawed. The suspensions were then combined with an equal volume of TEAN buffer, swirled gently to mix, and then centrifuged at 5,000 xg for 20 minutes at 4° C. to sediment membranes and unlysed cells. Typical recovery of LT-BNT from a single application of this freeze-thaw procedure was 50 percent. Further recovery could be made by either repeating the cycle or by applying other disruptive techniques to the more refractory unlysed cells. All supernatant fractions from the centrifugation steps were then combined for further purification.

Secretion of LT-BNT by S. Typhi SE12

Although *E. coli* strain JM83 (pJC217) produces large quantities of LT-BNT, more than 95% of the protein produced remains confined within the outer membrane. Thus, mechanical or other disruptive techniques must be used to free the LT-BNT produced by *E. coli*. In contrast, the *S. typhi* strain of this invention secretes a substantial part of its LT-BNT. This secretory capability is shown in Table 1.

The data of Table 1 were obtained by inoculating about $10^6$ SE12 cells in 125 ml Erlenmeyer flasks containing 20 ml of ML medium with or without 0.1% galactose. After 18 hours of incubation at 37° C., the medium was removed and the cells were lysed by sonication in TEAN buffer containing 0.05M Tris, 0.001M EDTA, 0.003M $NaN_3$, and 0.2M NaCl, pH 7.5. The LT-BNT present in both the cell lysate and in the medium was then quantified by ELISA analysis, as described in Section 6.2.1., supra.

TABLE 1

| | Distribution of LT-BNT Produced by S. typhi SE 12 | | |
|---|---|---|---|
| | LT-BNT (ng-ml of culture)* | | Percent |
| Medium | Cell Associated | Secreted | LT-BNT Secreted |
| ML | 2.51 ± 0.23 | 2.73 ± 0.17 | 52 |
| ML + 0.1% Galactose | 0.47 ± 0.21 | 3.65 ± 0.45 | 89 |

*± SEM

As shown in Table 1, approximately 50% of the LT-BNT produced by stain SE12 was secreted by the cells. When galactose was present in the medium, only 11% of the LT-BNT remained cell associated. Presumably this was the result of galactose-induced bacteriolysis.

Affinity Chromatographic Purification and Characterization of LT-BNT

Clear supernatant fluids from centrifuged cell lysates of E. coli JM83 (pJC217) or S. typhi SE12 were applied directly (not layered under buffer) to the top of a 2.5×80 cm Sepharose 4B [Pharmacia Fine Chemicals, Piscataway, N.J.] column which had previously been equilibrated in TEAN buffer at 4° C. The column was then purged with TEAN buffer at a flow rate of 20 ml per hour until effluent monitoring at 280 nm reached the baseline level. At that point, 0.2M galactose in TEAN buffer was applied and maintained at a flow rate of 20 ml per hour, while 6 ml fractions were collected. The emergence of LT-BNT was detected as a single peak of absorbance at 280 nm that slightly preceded the galactose front.

All operations were carried out at 4° C., and when complete, LT-BNT fractions were pooled, dialyzed against large volumes of TEAN buffer and lyophilized for storage.

Examination of the purified LT-BNTs by sodium dodecyl sulfate polyacrylamide gel electrophoresis by the method of Lwmmli [Nature 227: 680–685 (1970)] showed that the subunit from strain SE12 was indistinguishable from that produced by E. coli strain JM83 (pJC217). Both preparations contained only a single band with the mobility of the B subunit of LT, and no A subunit could be seen. Analysis by ELISA (Section 6.2.1) and by Ouchterlony immunodiffusion indicated that the preparations were immunologically identical.

Analysis of LT-BNT for Toxicity

Samples of LT, LT-B from clone pDF87, and LT-BNT from clone pJC217 were analyzed in the Y1 adrenal cell assay system as described supra, in Section 6.2.2. The protein content of the samples was determined by the method of Lowry et al. [J. Biol. Chem. 193:265–275 (1951)]. The results are shown in Table 2.

TABLE 2

| Adrenal Cell Assay of Enterotoxin Activity | |
|---|---|
| Preparation | Biological Activity* |
| LT | 0.038 |
| LT-B (pDF87) | 39 |
| LT-BNT (pJC217) | ND+ |

*Activity is expressed as the nanogram quantity of each preparation required to produce the rounding of 50% of the cells.
+ND = Not detectable with amounts up to 25,000 ng.

The data of Table 2 indicate that the toxicity of LT-BNT is drastically reduced compared to that of LT, with LT being greater than 650,000 times more active than LT-BNT. The results for LT-B show that it, while substantially less toxic than LT, retains considerable toxicity. This toxicity, which is comparable to that of the B subunit produced by the chromatographic separation of the complete LT enterotoxin into its subunits, renders ordinary LT-B unsuitable for use as a vaccine.

Analysis of LT and LT-BNT in the rat ileal loop assay, as described in seciton 6.2.3, also revealed the remarkable non-toxic character of LT-BNT. The results are shown in Table 3, wherein each value is the average from 5–8 rats.

TABLE 3

| Rat Ileal Loop Assay of Enterotoxin Activity | | |
|---|---|---|
| Preparation | Amount (ug) | Fluid Accumulation* Ratio (ul/cm of ileum) |
| LT | 1 | 65 |
| LT | 10 | 421 |
| LT | 100 | 818 |
| LT-BNT JM83 (pJC217) | 100 | 0 |
| LT-BNT SE12 | 100 | 0 |

*Fluid Accumulation Ratios greater than 50 are considered to be a positive result.

As shown in Table 3, a 100 ug quantity of LT-BNT was completely inactive in the rat ileal loop assay. This was true whether the LT-BNT was obtained from E. coli JM83 (pJC217) or from S. typhi SE12. In contrast, the same quantity of LT produced a stimulation of ileal loop fluid accumulation that was more than 16 times the minimally significant level.

The lack of toxicity in LT-BNT produced by S. typhi SE12 was further demonstrated in an experiment in which five guinea pigs (age, strain, source) were orally inoculated with $3 \times 10^9$ CFU of the strain. Observation of the animals for 14 days revealed no signs of diarrhea. All of the animals achieved normal weight gains and remained healthy throughout the period.

Preparation of Antiserum Against S. Typhi SE12

To demonstrate the effectiveness of strain SE12 as a vaccine, 4–6 week old female outbred CD1-1 mice (Charles River Breeding Laboratories, Wilmington, Ma.) were given intraperitoneal (i.p.) injections with $2.5 \times 10^7$ colony forming units (CFU)/ml of strain SE12 in 0.5 ml of sterile saline. After two weeks, some of the mice were boosted by i.p. injection of either $2.5 \times 10^7$ CFU of strain SE12 or 100 ug of affinity purified LT-BNT. Blood samples were taken periodically for up to four weeks following the primary vaccinations, and the sampels were analyzed by ELISA (Section 6.2.1). The results are shown in Table 4.

TABLE 4

| Vaccination of Mice with S. typhi Strain SE12 | | |
|---|---|---|
| Time After Primary Vaccination (days) | Second Vaccination | Antibody* Activity |
| 1 | — | ND |
| 3 | — | ND |
| 5 | — | 230 |
| 28 | — | 250 |
| 28 | SE12 | 4,500 |
| 28 | LT-BNT | 40,960 |

*ND = Not Detectable. Post-immune activity was measured in blood samples at the times indicated by alkaline phosphatase ELISA. Antibody activity is expressed as the reciprocal of the sample dilution giving an absorbance value of 1.0 at 405 nm. Each data point represents the pooled sera of 3–6 mice.

As shown in Table 4, SE12 produced a significant antitoxic antibody response which was specifically boosted either by the injection of additional SE12 cells or of purified LT-BNT from E. coli JM83 (pJC217). The antibody titer developed following two immunizations with strain SE12 was similar to that obtained in mice with two i.p. injections of 10 mg of purified LT-BNT administered two weeks apart.

In part, the efficacy of SE12 as a vaccine may be explained by the fact that the innoculated cells persist for a period of time in murine tissues. Essentially using the method of Formal et al. [Infect. Immun. 34: 746 (1981)], groups of female outbred CD-1 mice were injected i.p. with 0.5 ml of sterile saline containing $5 \times 10^7$ CFU/ml of either S. typhi strain Ty21a or SE12. At intervals of 1, 3, 5, 8, 10, 13 or 15 days after inoculation, groups of three animals were sacrificed and their spleens were aseptically removed and examined for the presence of bacteria.

To detect residual bacteria, the isolated spleens were homogenized, serially diluted and placed into Trypticase soy agar containing 100 mg/ml Ampicillin. After 72 hours of incubation at 37° C., the plates were scored for bacterial colonies.

These tests showed that both bacterial strains were present in the spleens one day after inoculation. By the third day, levels of strain Ty21a were reduced 10 fold, while strain SE12 was undetectable. By the fifth day and thereafter, strain Ty21a could also not be detected.

Deposit of Microorganism

The LT-BNT-producing S. typhi strain harboring plasmid PJC217 has been deposited with the American Type Culture Collection. Rockville, Md., and has been assigned accession number ATCC 39842. Cultures of this deposited microorganism will be made available to the pulbic upon the grant of a patent based upon the present application. The invention described and claimed herein is not to be limited in scope by the strain of microorganism deposited, since the deposited embodiment is intended only as an illustration of the invention. Any equivalent microorganisms that produce functionally equivalent enterotoxin subunits are within the scope of the invention.

I claim:

1. A stable avirulent strain of Salmonella typhi wherein said strain contains an expression vector having a DNA encoding the E. coli LT-B subunit of the heat labile enterotoxin of pJC217.

2. A pharmaceutical composition comprising a stable avirulent strain of Salmonella typhi of claim 1 having a DNA coding for the non-toxic polypeptide of the LT-B subunit of the heat-labile enterotoxin of Escherichia coli that is replicated, transcribed and translated, and a compatible pharmaceutical carrier thereof.

3. A pharmaceutical composition of claim 2, wherein the stable avirulent strain is the Salmonella typhi having ATCC accession number 39842.

4. The pharmaceutical composition of claim 2, wherein the stable avirulent strain is Salmonella typhi SE12.

5. The pharmaceutical composition of claim 2, wherein the pharmaceutical carrier is suitable for oral administration to human beings.

6. The pharmaceutical composition of claim 5, wherein the pharmaceutical carrier is a pharmaceutically acceptable electrolyte solution.

7. The pharmaceutical composition of claim 5, wherein said composition is a suspension in a pharmaceutically acceptable electrolyte solution.

8. The pharmaceutical composition of claim 5, wherein said composition is a suspension in milk.

* * * * *